United States Patent [19]

Bernstein

[11] Patent Number: 4,505,909

[45] Date of Patent: Mar. 19, 1985

[54] METHOD AND COMPOSITION FOR TREATING AND PREVENTING IRRITATION OF THE EYES

[76] Inventor: Joel E. Bernstein, 615 Brierhill Rd., Deerfield, Ill. 60015

[21] Appl. No.: 425,126

[22] Filed: Sep. 27, 1982

Related U.S. Application Data

[62] Division of Ser. No. 188,249, Sep. 17, 1980, Pat. No. 4,370,324.

[51] Int. Cl.$^3$ .................. A61K 31/33; A61K 31/335; A61K 31/135
[52] U.S. Cl. .................................. 514/217; 514/278; 514/450; 514/912; 514/656
[58] Field of Search ...................... 424/244, 278, 330

[56] References Cited

U.S. PATENT DOCUMENTS

| | | | |
|---|---|---|---|
| 3,705,942 | 12/1972 | Grunwaldt | 424/244 |
| 3,979,515 | 9/1976 | Allais et al. | 424/244 |
| 4,029,783 | 6/1977 | Wiedemann et al. | 424/244 |
| 4,124,583 | 11/1978 | Georgiev et al. | 424/244 |
| 4,138,482 | 2/1979 | Dostert | 424/244 |
| 4,181,655 | 1/1980 | Barton et al. | 424/244 |
| 4,186,184 | 1/1980 | Zaffaroni | 424/16 |

OTHER PUBLICATIONS

The Merck Index, 9th ed., (1976)–Merck & Co., items 8934 and 6192.

*Primary Examiner*—Douglas W. Robinson

[57] ABSTRACT

A method and composition for preventing and treating irritation of the eyes wherein a tricyclic anti-depressant applied to the eyes is effective to prevent irritation and a combination of the tricyclic anti-depressant with a vasoconstrictor is effective to prevent and to alleviate irritation of the eyes.

17 Claims, No Drawings

METHOD AND COMPOSITION FOR TREATING AND PREVENTING IRRITATION OF THE EYES

This is a division of application Ser. No. 188,249 filed Sept. 17, 1980, issued as U.S. Pat. No. 4,370,324 on Jan. 25, 1983.

BACKGROUND OF THE INVENTION

Allergic and irritant conditions of the conjunctivae and sclerae are quite common and are treated with sympathomimetic amines applied locally to produce vasoconstriction of local blood vessels. Such irritation or allergies of the mucous membranes of the eyes may follow accidental introduction of foreign particles or may be part of the allergic manifestations of asthma, hayfever, and allergic rhinitis.

While there are a limited number of vasoconstrictive compounds available for treating irritation of the eye there are no compounds available for preventing irritation of the eye due to irritant and/or allergic conditions, that is there is no prophylactic treatment available.

I have discovered that tricyclic anti-depressants usually prescribed for ameliorating the effects of severe depression are prophylactically effective when applied topically to prevent irritation of the eyes upon exposure to irritant conditions. These tricyclic anti-depressants have little effect on the treatment of already irritated eyes, but when combined with known vasoconstrictors are effective for preventing future irritations while effectively treating present irritation.

SUMMARY OF THE DISCLOSURE

The present invention relates to a method and composition for preventing and treating irritation of the eyes.

A principal object of the present invention is to provide a method and composition for preventing irritation of the eyes due to allergic or irritant conditions comprising applying to the eyes a therapeutically effective amount of a tricyclic anti-depressant.

Another object of the present invention is to provide a method and composition for preventing and treating irritation of the eyes due to allergic or irritant conditions comprising periodically applying to the eyes a therapeutically effective amount of a tricyclic anti-depressant and a vasoconstrictor.

Yet another object of the present invention is to provide a method and composition for treating and preventing irritation of the eyes wherein the tricyclic anti-depressant contains one of the following ring structures:

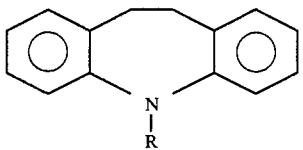

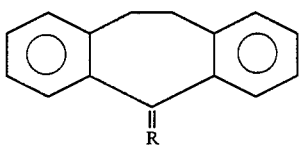

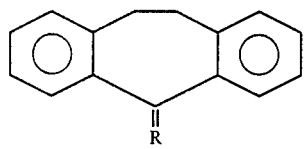

and also includes a viscosity adjusting composition, a preservative and a buffering agent.

These and other objects of the present invention may be more readily understood when considered in conjunction with the following detailed description and examples.

DETAILED DESCRIPTION OF THE PREFERRED EMBODIMENTS

I investigated the possible local effects of tricyclic anti-depressant compounds usually used to ameliorate severe depression by instilling varying concentrations of these agents into the eyes of albino rabbits before and after instillation of 5–10% by weight solutions of sodium lauryl sulfate (SLS) in an aqueous/alcohol vehicle. The instillation of 5–10% by weight SLS solution produces marked irritation and injection of the rabbit sclerae and conjunctivae. Surprisingly, instillation of 0.05% by weight to 1% by weight of imipramine hydrochloride, amitriptyline hydrochloride, and doxepin hydrochloride protects the eye from the irritant effects of the SLS solution. However, these solutions provide only a little decrease in the eye irritation when instilled after irritation has been produced. When similar concentrations of these tricyclic anti-depressant compounds are combined with concentrations of 0.01% by weight to 0.05% by weight of known vasoconstrictors, such as naphazoline hydrochloride or tetrahydrozaline hydrochloride, the resulting opthalmic drops both reverse previously induced irritation and also render the eyes refractory to SLS for hours.

In the practice of this invention, eye drops are prepared employing 0.05% by weight to 1% by weight concentrations of the category of pharmacological agents known as the tricyclic anti-depressants, such as doxepin, amitriptyline and imipramine hydrochloride, respectively a tertiary amine derivative of dibenzoxepin, dibenzocycloheptadiene and dibenzazepine, in aqueous vehicles containing 0.05% hydroxypropyl methylcellulose as a viscosity adjusting agent, 0.01% benzalkonium chloride or 0.01% edetate sodium as preservatives and boric acid, sodium carbonate, and sodium hydroxide as buffering agents. Such eye drops are instilled from one to four times daily to prevent symptoms of eye irritation or allergy. Inclusion of known vasoconstrictor agents such as 0.01 to 0.05% naphazolixe hydrochlorides or tetrahydrozaline hydrochloride allows such drops to be used both prophylactically as well as therapeutically to relieve and prevent such eye irritation.

EXAMPLE I

A 0.05% doxepin hydrochloride solution containing 0.5% hydroxypropyl methlcellulose, 0.01% benzalkonium chloride, 1% sodium chloride and sodium carbonate and boric acid (utilized as buffers to adjust solution to a pH of 7.4) was instilled in the eyes of 5 albino rabbits. Five minutes after instillation of such drops, a 10% sodium lauryl sulfate (SLS) solution was instilled in the rabbits' eyes. No injection of the sclerae or conjunctivae was noted during 30 minutes of observation.

EXAMPLE II

A 1.0% solution of amitriptyline hydrochloride containing 1.0% hydroxymethlcellulose, 0.1% edetate sodium, 1% potassium chloride, titrated with sodium borate and sodium hydroxide to a pH of 7.2 was instilled into the eyes of 5 albino rabbits 10 minutes prior to the introduction of 10.0% SLS into the rabbits' eyes. No eye irritation was noted in the 60 minutes of observation.

EXAMPLE III

A 0.5% solution of doxepin hydrochloride containing 2.5% hydroxypropyl methylcellulose, 0.004% benzalkonium chloride, 2.0% sodium chloride and sodium citrate and sodium carbonate as buffers (titrating eye drops to pH of 7.6) was instilled into the eyes of 4 albino rabbits. In 2 rabbits the drops were instilled 10 minutes before instillation of a 5% SLS solution and in the other 2, the drops were instilled 60 minutes after instillation of a 10% SLS solution. Instillation of the drops before the SLS prevented eye irritation. However, instillation after SLS had produced eye irritation resulted in no change or improvement in the eye irritation.

EXAMPLE IV

A 0.05% imipramine hydrochloride solution containing 0.01% hydroxymethylcellulose, thimerosal 0.005%, sodium chloride 0.5% (buffered to pH 7.0 with boric acid and sodium carbonate) was instilled into the eyes of 4 albino rabbits. Two rabbits received the eye drops 15 minutes before the instillation of 10% SLS, while 2 received the drops 90 minutes after the SLS was instilled. No irritation was observed in one rabbits' eyes and only mild irritation in the other rabbits' eyes, both of which had received the eye drops before SLS. The rabbits receiving SLS first had markedly irritated eyes with sclerae and conjunctival injection and this was not affected by the later instillation of the imipramine drops.

EXAMPLE V

A 0.05% amitriptyline hydrochloride solution, with 2.5% hydroxymethylcellulose, 0.01% edetate sodium, 0.5% sodium chloride, buffered to pH 7.4 by boric acid and sodium hydroxide, was instilled into the eyes of 5 rabbits on two separate days, on one day 10 minutes before the instillation of 10% SLS, while on the other day 60 minutes after SLS instillation. The amitriptyline drops prevented eye irritation from the SLS but had no effect on the irritation when instilled after the SLS.

EXAMPLE VI

An aqueous solution containing 1.0% doxepin hydrochloride, 0.05% naphazoline hydrochloride, 0.01% hydroxymethylcellulose, 0.004% benzalkonium chloride, 1.0% sodium chloride, buffered with sodium borate to pH 7.4 was instilled into the eyes of 5 albino rabbits on two different days. On one day the eye drops were instilled 10 minutes before the instillation of a 10% SLS solution and on the other day they were instilled 60 minutes after 10% SLS instillation. In the former case the drops prevented SLS-induced eye irritation, while in the latter the SLS-induced eye irritation was markedly reduced within =minutes and re-instillation of 10% SLS did not irritate the eyes again.

EXAMPLE VII

An aqueous solution of 0.05% amitriptyline hydrochloride and 0.01% naphazoline hydrochloride with 0.01% hydroxypropyl methylcellulose, 0.1% edetate sodium, 1% potassium chloride, buffered to pH 7.2 with boric acid and sodium hydroxide, was instilled into the eyes of 5 rabbits as described in Example VI. Prior instillation of these drops prevented or markedly reduced SLS induced eye irritation, while instillation after such irritation had been produced rapidly (within 5 minutes) reduced such irritation.

EXAMPLE VIII

A 0.01% amitriptyline hydrochloride solution containing 0.01% tetrahydrozaline hydrochloride, 0.01% hydroxymethycellulose, 0.01% benzalkonium chloride, 0.5% sodium chloride, buffered to pH 7.4 with sodium hydroxide and sodium citrate, was instilled as described in Example VI into the eyes of 5 rabbits on two separate occasions. Prior instillation of these drops prevented eye irritation from 10% SLS, while instillation after SLS-induced eye irritation, both relieved such irritation and prevented irritation from re-instillation of 10% SLS.

EXAMPLE IX

A 0.05% doxepin hydrochloride solution identical in composition to Example I but also containing 0.05% tetrahydrozaline hydrochloride was instilled into 4 rabbits eyes before and after SLS instillation on 2 different occasions. Prior instillation of these drops prevented or markedly reduced eye irritation in the rabbits' eyes. Instillation 60 minutes after SLS irritation was induced resulted in a prompt (within 10 minutes) clearing of the eyes and prevented irritation from the re-instillation of 10% SLS.

The tertiary amines have the following chemical formulas:

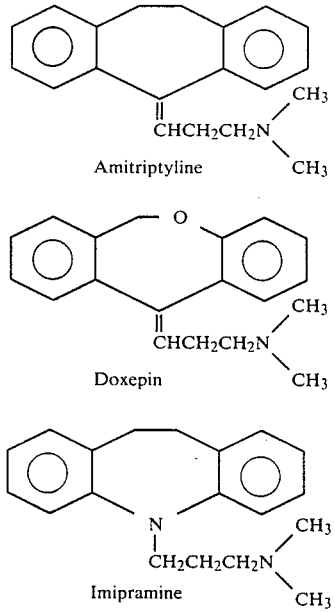

In addition, the secondary amines of the before mentioned tricyclics are effective and are included within the scope of this invention. Secondary amines include Nortriptyline, Protriptyline and Desipramine, respectively derivatives of dibenzocycloheptadiene, dibenzoxepin and dibenzazepine, and have the following chemical formulas:

Nortriptyline

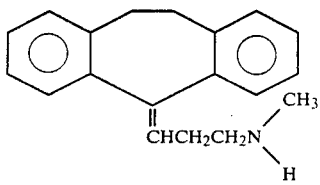

Protriptyline

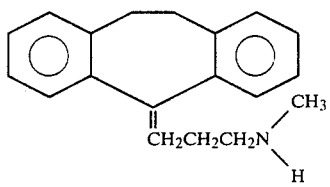

Desipramine

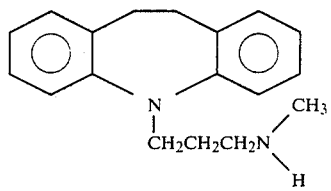

What is claimed is:

1. A method of preventing and treating irritation of the mucous membranes of the eye caused by allergies, chemical pollutants, or physical irritants, manifested by redness, tearing, burning, discomfort or itching, comprising applying topically to said eye a therapeutically effecive amount of a tricyclic anti-depressant selected from the group consisting of:

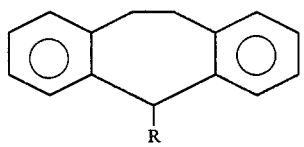

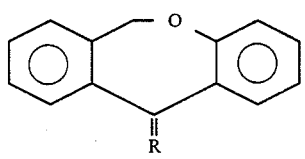

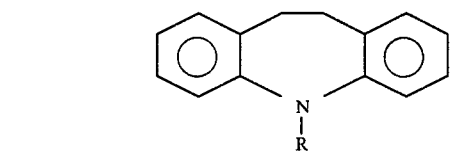

wherein R is an aliphatic secondary or tertiary amine having a three-aliphatic carbon chain connected to a nitrogen atom, with the seondary amine having the nitrogen atom attached to said chain and to one carbon atom, and with the tertiary amine having the nitrogen atom attached to said chain and to two carbon atoms; and a therapeutically effective amount of an ophthalmically acceptable vasoconstrictor.

2. The method of claim 1, wherein the tricyclic anti-depressant and the vasoconstrictor are present in an aqueous carrier, the concentration of the tricyclic anti-depressant in the carrier being not less than about 0.05% by weight of the carrier and the concentration of the vasoconstrictor in the carrier being not less than about 0.01% by weight of the carrier.

3. The method of claim 2, wherein the vasconstrictor is present in the range of between about 0.01% by weight and about 0.05% by weight of the carrier.

4. The method of claim 2, wherein the anti-depressant is present in the range of between about 0.05% by weight and about 1% by weight of the carrier.

5. The method of claim 1, wherein the vasoconstrictor is naphazoline hydrochloride or tetrahydrozaline hydrochloride.

6. The method of claim 5, further comprising a viscosity adjusting agent, a preservative of benzalkonium chloride or edetate sodium and a buffering agent selected from boric acid, sodium carbonate, sodium hydroxide, or mixtures thereof.

7. The method of claim 6, wherein said viscosity adjusting agent is hydroxypropyl methylcellulose.

8. An ophthalmic composition for preventing and treating irritation of the mucous membrane of the eyes caused by allergies, chemical pollutants, or physical irritants, manifested by redness, tearing, burning discomfort, or itching, comprising a therapeutically effective amount of a tricyclic anti-depressant selected from the group consisting of:

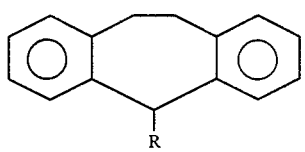

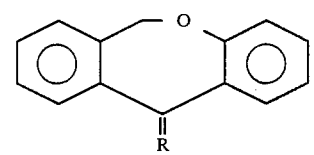

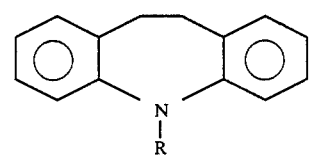

wherein R is an aliphatic secondary or teritary amine having an aliphatic 3 carbon chain connected to a nitrogen atom, with the secondary amine having the nitrogen atom attached to said chain and to one carbon atom attached and with the teritary amine having the nitrogen atom attached to said chain and to two carbon atoms and an ophthalmically acceptable vasoconstrictor, said tricyclic anti-depressant and said vasoconstrictor in an ophthalmically suitable fluid carrier having an ophthalmically acceptable preservative and buffering agent suitable to maintain said composition at a pH in excess of 7.

9. The composition of claim 8, wherein the tricyclic anti-depressant and the vasoconstrictor are present in an aqueous carrier, the concentration of the tricyclic anti-depressant in the carrier being not less than about 0.05% by weight of the carrier and the concentration of the vasoconstrictor in the carrier being not less than about 0.01% by weight of the carrier.

10. The composition of claim 9, wherein the vasoconstrictor is present in the range of between about 0.01% by weight and about 0.05% by weight of the carrier.

11. The composition of claim 9, wherein the anti-depressant is present in the range of between about 0.05% by weight and about 1% by weight of the carrier.

12. The composition of claim 8, wherein the vasoconstrictor is naphazoline hydrochloride or tetrahydrozaline hydrochloride.

13. The composition of claim 12, wherein said composition further comprises a viscosity adjusting agent, a preservative of benzalkonium chloride or edtate sodium and a buffering agent selected from boric acid, sodium carbonate, sodium hydroxide, or mixtures thereof.

14. The composition of claim 13, wherein the tricyclic anti-depressant is selected from the class consisting of dibenzazepine, dibenzocycloheptadiene, dibenzoxepin, and derivatives thereof.

15. The composition of claim 13, wherein the tricyclic anti-depressant is selected from the class consisting of imipramine hydrochloride, amitriptyline hydrochloride and doxepin hydrochloride.

16. The composition of claim 13, wherein the tricyclic anti-depressant is selected from the class consisting of nortriptyline, protriptyline, and desipramine.

17. The composition of claim 13, wherein said viscosity adjusting agent is hydroxypropyl methylcellulose.

* * * * *

UNITED STATES PATENT AND TRADEMARK OFFICE
CERTIFICATE OF CORRECTION

PATENT NO. : 4,505,909

DATED : March 19, 1985

INVENTOR(S) : Joel E. Bernstein

It is certified that error appears in the above-identified patent and that said Letters Patent is hereby corrected as shown below:

Column 1, line 6, insert "since" before --issued--;

Column 1, line 63, insert a circle on top of center ring in second picture;

Column 3, line 67, replace " ≡ with --5--;

Column 5, line 66, replace "seondary" with --secondary--;

Signed and Sealed this

Twenty-fourth Day of December 1985

[SEAL]

Attest:

DONALD J. QUIGG

Attesting Officer

Commissioner of Patents and Trademarks